United States Patent [19]

Holtkamp

[11] Plant 4,416

[45] May 15, 1979

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 880,212

[22] Filed: Feb. 22, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An african violet referred to by the cultivar name Michigan having dark green foliage and generally pink flowers which are non-dropping and have excellent color retention. The flowers are carried on short peduncles on straight and upright stems. The plant has a vigorous, compact and fast growing habit, with the first flash of flowers appearing 8-10 weeks after potting.

1 Drawing Figure

The present invention comprises a new and distinct cultivar of african violet plant, botanically known as *Saintpaulia ionantha,* and referred to by the cultivar name Michigan. Michigan was identified during the breeding and selection process by the numbers 165/5 and 43/77, and is a product of a planned breeding program. Michigan is principally characterized by its large pink non-dropping flowers, straight flower stems, short and upright peduncles, and an abundance of flowers which produce a rich and full bouquet above the rosette of leaves.

The new cultivar was originated from a cross made in a controlled breeding program in Isselburg, Rhineland, Germany. The female, or seed parent, is unpatented and identified as XIX 4208 pink (RHS 62 A). The male, or pollen parent, is also unpatented and identified for breeding purposes by the designation BKS VII.

Michigan was selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeated observed and are determined to be basic characteristics of Michigan, which in combination distinguish this african violet as a new and distinct cultivar:

(1) Straight and upright flower stems.

(2) 6-9 flower stems when the plant first blooms.

(3) The stems each carry up to 8 flowers and buds on short peduncles, with the flower being generally pink in flower color, non-dropping and possessing excellent color retention.

(4) The plant first blooms 8-10 weeks after potting, and is in full bloom in 10-12 weeks.

(5) Very vigorous and fast growing, and compact habit.

(6) Dark green foliage.

The accompanying photographic drawing shows a typical specimen plant of the new cultivar. The colors appearing in the photograph are as true as possible with color illustrations of this type.

In the following description, flower color values are referenced to Horticultural Color Chart (Wilson), and the color values of foliage, buds, sepals, and reproductive organs are referenced to RHS Color Chart, 1966 edition. It is noted that is was difficult to obtain exact color values for the flowers, and the color values indicated below are as accurate as possible.

Botanical classification: *Saintpaulia ionantha,* Ramat. cv Michigan.

Parentage:

*Male parent.*—BKS VII.

*Female parent.*—XIX 4208 pink.

Propagation: The new cultivar holds its distinguishing characteristics through successive propagations by leaf cuttings and by division of shoots.

Plant: From 9 cm. to 11 cm. tall when grown in pots, and approximately 25 cm. in diameter when fully grown.

Leaves:

*General form.*—Oblong.

*Diameter.*—50-60 mm.

*Texture.*—soft.

*Veins.*—Well pronounced, red-brown.

*Color (upperside).*—147 A, dark green.

*Color (underside).*—187 D, purple.

*Petiole.*—red.

Flowers:

*Buds.*—Round shape, diameter 5-7 mm., color 13 D.

*Sepals.*—Five, 4-5 mm. long, spearshaped. Color: 199 A. Calyx: Peduncle and seed vessel fused. Aspect: funnel-shaped. Peduncle: straight and up to 22 mm. long.

Individual flowers:

*Size.*—Total flower diameter 35-40 mm., with the three large petals being 17-18 mm. long and 14-15 mm. wide, and the two small petals being 12-13 mm. long and 10-11 mm. wide.

*Color.*—Upperside: Between 630 and 630/1. Underside: Between 630/2 and 630/3.

*Borne.*—Up to 9 flowers on each flower stem.

*Shape.*—Five petals, two small, three large.

*Arrangement.*—Strong, straight flower stems with up to 8 flowers on short peduncles.

*Flowering time.*—The plant is in bloom 8–10 weeks after potting, and is in full bloom in 10–12 weeks following potting.

Reproductive organs:

*Stamens.*—Two in number.

*Anthers.*—Four anthers, color 7 A; close together.

*Arrangement.*—The stamens are joined with two stems to the receptacle underneath the seed vessel.

*Filaments.*—3 mm. long.

*Styles.*—7–8 mm. long, color 64 A.

*Pollen color.*—7 C.

Roots: Well spreading roots; the young roots are white, the older ones are brownish.

Disease resistance: No disease problems noticed to date.

General observations: Michigan is a very fast and vigorous growing african violet. When blooming for the first time, it shows 6–9 strong, straight flower stems with up to 8 single flowers on short peduncles. The color retention of the flowers is excellent, and the flowers dry when mature, rather than drop. The foliage is dark green and contrasts well with the full flower bouquet above the rosette of leaves.

I claim:

1. A new and distinct cultivar of african violet referred to by the cultivar name Michigan and characterized by the combined features of generally pink flowers which are non-dropping and have excellent color retention, the flowers being carried on short peduncles on straight and upright stems; vigorous, compact and fast growing habit, with the first flash of flowers appearing 8–10 weeks after potting, and by its dark green foliage.

* * * * *

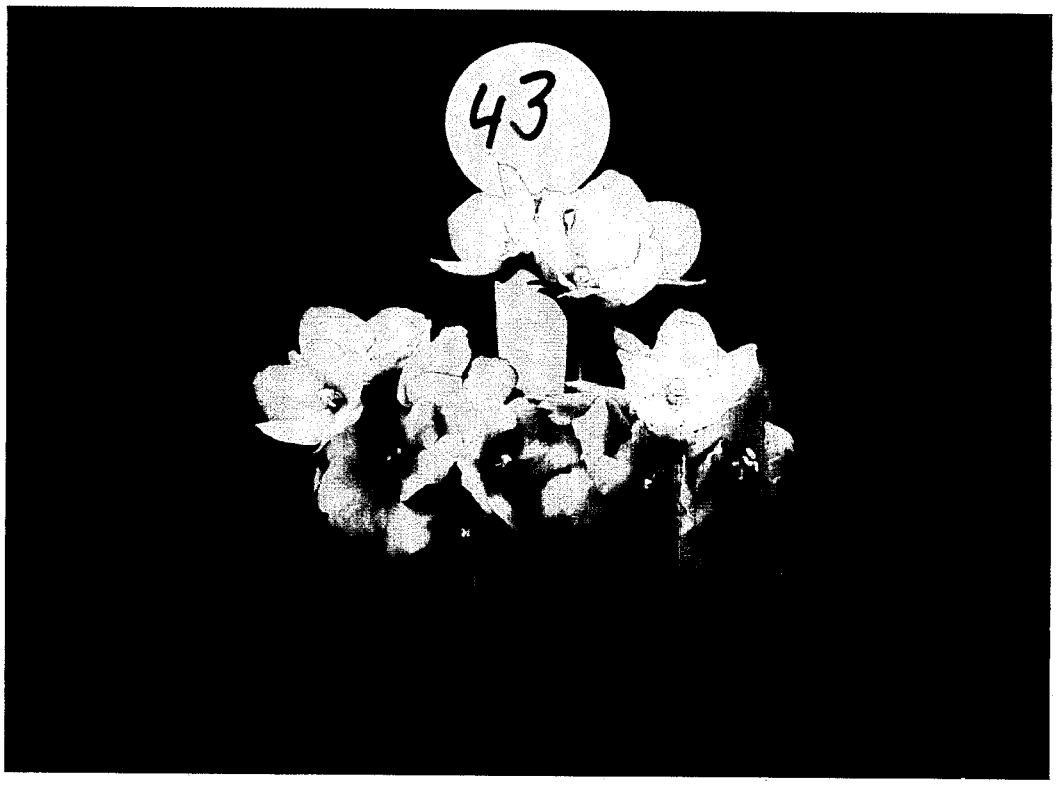
43